US008764665B2

(12) United States Patent
Hall et al.

(10) Patent No.: US 8,764,665 B2
(45) **Date of Patent: *Jul. 1, 2014**

(54) METHODS AND APPARATUSES OF MICROBEAMFORMING WITH ADJUSTABLE FLUID LENSES

(75) Inventors: Christopher Stephen Hall, Hopewell Junction, NY (US); Chien Ting Chin, Tarrytown, NY (US); Jan Frederik Suijver, Dommelen (NL); Bernardus Hendrikus Wilhelmus Hendriks, Eindhoven (NL); Stein Kuiper, Neerijnen (NL)

(73) Assignee: Koninklijke Philips N.V., Eindhoven (NL)

( * ) Notice: Subject to any disclaimer, the term of this patent is extended or adjusted under 35 U.S.C. 154(b) by 922 days.

This patent is subject to a terminal disclaimer.

(21) Appl. No.: 12/596,841

(22) PCT Filed: Apr. 30, 2008

(86) PCT No.: PCT/IB2008/051686

§ 371 (c)(1),
(2), (4) Date: Oct. 21, 2009

(87) PCT Pub. No.: WO2008/135922

PCT Pub. Date: Nov. 13, 2008

(65) Prior Publication Data

US 2010/0087735 A1 Apr. 8, 2010

Related U.S. Application Data

(60) Provisional application No. 60/915,703, filed on May 3, 2007.

(51) Int. Cl.
*A61B 8/00* (2006.01)

(52) U.S. Cl.
USPC ........... 600/459; 600/443; 359/666; 367/138; 73/642

(58) Field of Classification Search
USPC .............. 600/437, 443, 444, 459, 467; 367/7, 367/138; 257/98, 294, E33.068, E33.073; 73/642
See application file for complete search history.

(56) References Cited

U.S. PATENT DOCUMENTS 5,477,736 A * 12/1995 Lorraine ......................... 73/642
6,554,826 B1 4/2003 Deardorff (Continued)

FOREIGN PATENT DOCUMENTS

DE 19704940 1/1998
WO WO03069380 8/2003

(Continued)

*Primary Examiner* — Unsu Jung
*Assistant Examiner* — Amanda Lauritzen Moher

(57) ABSTRACT

An acoustic probe (100, 300) includes an acoustic transducer (15, 444), and a plurality of variably-refracting acoustic lens elements (10, 210*a*, 210*b*, 442) coupled to the acoustic transducer. Each variably-refracting acoustic lens element has at least a pair of electrodes (150, 160) adapted to adjust at least one characteristic of the variably-refracting acoustic lens element in response to a selected voltage applied across the electrodes. In one embodiment, each variably-refracting acoustic lens element includes a cavity, first and second fluid media (141, 142) disposed within the cavity, and the pair of electrodes. The speed of sound of an acoustic wave in the first fluid medium is different than the speed of sound of the acoustic wave in the second fluid medium. The first and second fluid media are immiscible with respect to each other, and the first fluid medium has a substantially different electrical conductivity than the second fluid medium.

23 Claims, 6 Drawing Sheets

(56) References Cited

U.S. PATENT DOCUMENTS

| | | | | |
|---|---|---|---|---|
| 6,904,070 | B2 * | 6/2005 | Pontis et al. | 372/38.07 |
| 7,446,945 | B2 * | 11/2008 | Kuiper et al. | 359/666 |
| 7,957,219 | B2 * | 6/2011 | Hall et al. | 367/7 |
| 8,233,221 | B2 * | 7/2012 | Suijver et al. | 359/665 |
| 2010/0280390 | A1 * | 11/2010 | Hendriks et al. | 600/467 |
| 2011/0178391 | A1 * | 7/2011 | Fernandez et al. | 600/411 |
| 2012/0105645 | A1 * | 5/2012 | Burcher et al. | 348/163 |

FOREIGN PATENT DOCUMENTS

| | | | | |
|---|---|---|---|---|
| WO | WO2004051323 | | 6/2004 | |
| WO | WO2005122139 | | 12/2005 | |
| WO | WO 2008/023287 | * | 2/2008 | G10K 11/30 |

* cited by examiner

METHODS AND APPARATUSES OF MICROBEAMFORMING WITH ADJUSTABLE FLUID LENSES

CROSS REFERENCE TO RELATED CASES

Applicants' International Application Number PCT/IB2008/051686, filed Apr. 30, 2008 claims the benefit of U.S. Provisional Application Ser. No. 60/915,703, filed May 3, 2007. The present application is the U.S. national stage of International Application Number PCT/IB2008/051686, filed Apr. 30, 2008.

This invention pertains to acoustic imaging methods, acoustic imaging apparatuses, and more particularly to methods and apparatuses for elevation focus control for acoustic waves employing an adjustable fluid lens.

Acoustic waves (including, specifically, ultrasound) are useful in many scientific or technical fields, such as medical diagnosis, non-destructive control of mechanical parts and underwater imaging, etc. Acoustic waves allow diagnoses and controls which are complementary to optical observations, because acoustic waves can travel in media that are not transparent to electromagnetic waves.

Acoustic imaging equipment includes both equipment employing traditional one-dimensional ("1D") acoustic transducer arrays, and equipment employing fully sampled two-dimensional ("2D") acoustic transducer arrays employing microbeamforming technology.

In equipment employing a 1D acoustic transducer array, the acoustic transducer elements are often arranged in a manner to optimize focusing within a single plane. This allows for focusing of the transmitted and received acoustic pressure wave in both axial (i.e. direction of propagation) and lateral dimensions (i.e. along the direction of the 1D array).

Several technological solutions to this problem have been proposed including increased element count (1.5D arrays, 2D arrays) or adjustable lens material (rheological delay structures) but each has been less than universally accepted. Increasing the element count can only be successful if each element is individually addressable—increasing the cost of the associated electronics enormously. Adjustable delays such as a rheological material have less than optimal solution because of the added need to adjust the delay separately above each element—also adding complexity.

Meanwhile, one of the key enabling aspects to allow the manufacturing of fully sampled 2D acoustic transducer arrays is microbeamforming technology. This solution involves the use of electronic delay and sum circuitry in the form of application specific integrated circuits (ASICs) mounted immediately on the acoustic transducer array. These ASICS are tied to many elements in order to adjust the time delay and sum of "patched" or grouped elements. This effectively allows many elements to be reduced logically to a single, adjustable focus element, thereby reducing the number of cables necessary to return from the acoustic transducer to the driving and receive electronics, while maintaining the high element count necessary to meet a $\lambda/2$ criteria to minimize grating lobes. This technology has been successfully deployed in commercial acoustic transducers, but adds the complexity and costs of additional electronics and interconnects.

Accordingly, it would be desirable to provide an acoustic imaging device which provides the functionality of a 2D microbeamformer array, but which requires less electronics, fewer elements and potentially could be much cheaper to deploy. It would be particularly desirable to provide such an acoustic imaging device with a large active transducer aperture, where a fully sampled (elements<half a wavelength) transducer would be cost prohibitive.

In one aspect of the invention, an acoustic imaging apparatus comprises: an acoustic probe, including, an acoustic transducer, and a plurality of variably-refracting acoustic lens elements coupled to the acoustic transducer, each variably-refracting acoustic lens element having at least a pair of electrodes adapted to adjust at least one characteristic of the variably-refracting acoustic lens element in response to a selected voltage applied across the electrodes thereof; an acoustic signal processor coupled to the acoustic transducer; a variable voltage supply adapted to apply selected voltages to the pair of electrodes of each variably-refracting acoustic lens; and a controller adapted to control the variable voltage supply to apply the selected voltages to the pairs of electrodes.

In yet another aspect of the invention, an acoustic probe comprises: an acoustic transducer; and a plurality of variably-refracting acoustic lens elements coupled to the acoustic transducer, each variably-refracting acoustic lens element having at least a pair of electrodes adapted to adjust at least one characteristic of the variably-refracting acoustic lens element in response to a selected voltage applied across the electrodes.

In still another aspect of the invention, a method of performing a measurement using acoustic waves comprises: (1) applying an acoustic probe to a patient; (2) controlling a plurality of variably-refracting acoustic lens elements of the acoustic probe to focus in a desired elevation focus; (3) receiving from the variably-refracting acoustic lens elements, at an acoustic transducer, an acoustic wave back coming from a target area corresponding to the desired elevation focus; and (4) outputting from the acoustic transducer an electrical signal corresponding to the received acoustic wave.

FIGS. 1A-B show one embodiment of an acoustic probe including a plurality of variably-refracting acoustic lenses each coupled to a corresponding acoustic transducer.

FIGS. 2A-C illustrate some possible arrangements of variably-refracting acoustic lens arrays.

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided as teaching examples of the invention.

Variable-focus fluid lens technology is a solution originally invented for the express purpose of allowing light to be focused through alterations in the physical boundaries of a fluid filled cavity with specific refractive indices (see Patent Cooperation Treat (PCT) Publication WO2003/069380, the entirety of which is incorporated herein by reference as if fully set forth herein). A process known as electro-wetting, wherein the fluid within the cavity is moved by the application of a voltage across conductive electrodes, accomplishes the movement of the surface of the fluid. This change in surface topology allows light to be refracted in such a way as to alter the travel path, thereby focusing the light.

Meanwhile, ultrasound propagates in a fluid medium. In fact the human body is often referred to as a fluid incapable of supporting high frequency acoustic waves other than compressional waves. In this sense, the waves are sensitive to distortion by differences in acoustic speed of propagation in bulk tissue, but also by abrupt changes in speed of sound at interfaces. This property is exploited in embodiments of an acoustic probe and an acoustic imaging apparatus as disclosed below. In the discussion to follow, description is made of an acoustic imaging apparatus and an acoustic probe including a variably-refracting acoustic lens. In the context of the term "variably-refracting acoustic lens" as used in this application, the word "lens" is defined broadly to mean a device for directing or focusing radiation other than light (possibly in addition to light), particularly acoustic radiation, for example ultrasound radiation. While a variably-refracting acoustic lens may focus an acoustic wave, no such focusing is implied by the use of the word "lens" in this context. In general, a variably-refracting acoustic lens as used herein is adapted to refract an acoustic wave, which may deflect and/or focus the acoustic wave.

Figure 1A:
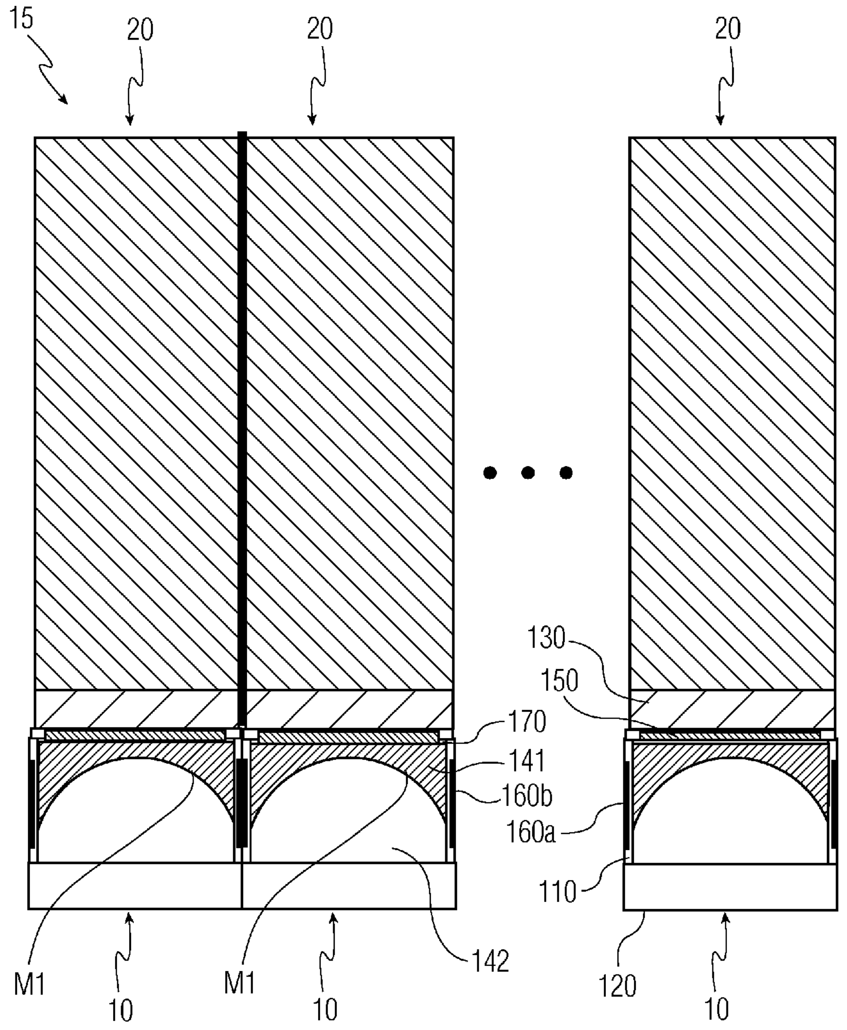
Figure 1B:
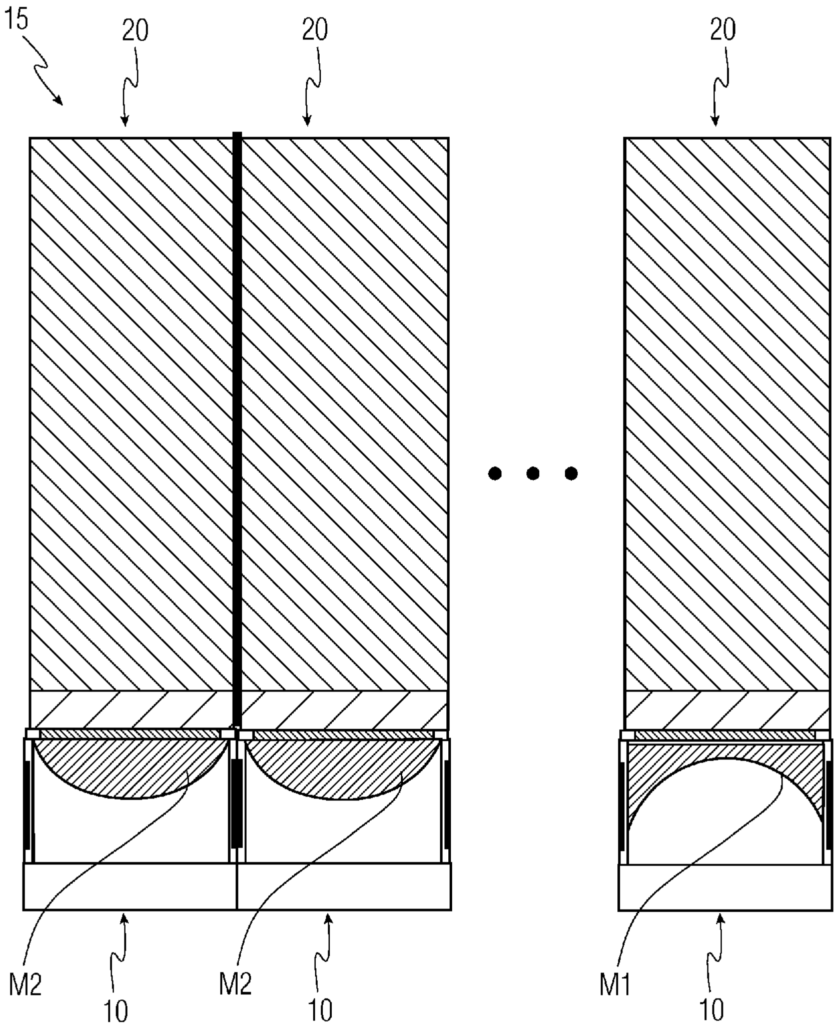

FIGS. 1A-B show one embodiment of an acoustic probe 100 comprising an array of variably-refracting acoustic lens elements 10 each coupled to a corresponding one of a plurality of acoustic transducer elements 20 of an acoustic transducer 15. Variably-refracting acoustic lens elements 10 are each adapted to adjust at least one acoustic signal processing characteristic thereof in response to at least one selected voltage applied thereto. For example, beneficially each variably-refracting acoustic lens element 10 includes the ability to vary the focus of an acoustic wave along the axis of propagation ("focus"), and/or perpendicular to this axis ("deflection"), as described in greater detail below. Each variably-refracting acoustic lens element 10 includes a housing 110, a coupling element 120, first and second fluid media 141 and 142, first electrode 150, and at least one second electrode 160*a*. Housing 110 may be of cylindrical shape, for example. Beneficially, the top end and bottom end of housing 110 are substantially acoustically transparent, while the acoustic waves do not penetrate through the side wall(s) of housing 110. A corresponding acoustic transducer element 20 is coupled to the bottom of housing 110, beneficially by one or more acoustic matching layers 130. The need for the acoustic matching layer is driven primarily by the choice of acoustic transducer material and may not be necessary in some implementations, as is the case with piezoelectric micromachined ultrasound transducers (PMUTs) or capacitive micromachined ultrasound transducers (CMUTs).

Acoustic transducer elements 20 may comprise a 1D array or even a 2D array.

Beneficially, as explained in greater detail below, the combination of variably-refracting acoustic lens elements 10 coupled to acoustic transducer elements 20 can emulate a microbeamforming 2D acoustic transducer array. In that case, each acoustic transducer element 20 replaces many (e.g., 16) acoustic transducer elements in a traditional microbeamforming 2D acoustic transducer array. For example, the operation of an acoustic probe having a traditional microbeamforming 2D array of 64×64=4096 elements, may be replaced by the acoustic probe 100 having only 256 acoustic transducer elements 20, and 256 variably-refracting acoustic lens elements 10. Because the element size is larger than a fully sampled array, the appearance of grating lobes would normally be a technical challenge. However, with the introduction of the lens in front of each large element, the same steering capabilities of a smaller element array can be accomplished. Beneficially, acoustic probe 100 requires less electronics, fewer elements and potentially could be much cheaper to deploy than an acoustic probe employing a traditional microbeamforming 2D acoustic transducer array.

In one embodiment, acoustic probe 100 is adapted to operate in both a transmitting mode and a receiving mode. In that case, in the transmitting mode each acoustic transducer element 20 converts electrical signals input thereto into acoustic waves which it outputs. In the receiving mode, each acoustic transducer element 20 converts acoustic waves which it receives into electrical signals which it outputs. Acoustic transducer element 20 is of a type well known in the art of acoustic waves.

In an alternative embodiment, acoustic probe 100 may instead be adapted to operate in a receive-only mode. In that case, a transmitting transducer is provided separately.

In yet another embodiment, the acoustic probe 100 may instead be utilized in a transmit only mode. Such a mode would be useful for therapeutic applications where ultrasound is intended to interact with tissue or the insonified object to deliver a therapy.

Beneficially, coupling element 120 is provided at one end of housing 110. Coupling element 120 is designed for developing a contact area when pressed against a body, such as a human body. Beneficially, coupling element 120 comprises a flexible sealed pocket filled with a coupling solid substance such as a Mylar film (i.e., an acoustic window) or plastic membrane with substantially equal acoustic impedance to the body.

Housing 110 encloses a sealed cavity having a volume V in which are provided first and second fluid media 141 and 142. In one embodiment, for example the volume V of the cavity within housing 110 is about 0.8 cm in diameter, and about 1 cm in height, i.e. along the axis of housing 110.

Advantageously, the speeds of sound in first and second fluid media 141 and 142 are different from each other (i.e., acoustic waves propagate at a different velocity in fluid medium 141 than they do in fluid medium 142). Also, first and second fluid medium 141 and 142 are not miscible with each another. Thus they always remain as separate fluid phases in the cavity. The separation between the first and second fluid media 141 and 142 is a contact surface or meniscus which defines a boundary between first and second fluid media 141 and 142, without any solid part. Also advantageously, one of the two fluid media 141, 142 is electrically conducting, and the other fluid medium is substantially non-electrically conducting, or electrically insulating.

In one embodiment, first fluid medium 141 consists primarily of water. For example, it may be a salt solution, with ionic contents high enough to have an electrically polar behavior, or to be electrically conductive. In that case, first fluid medium 141 may contain potassium and chloride ions, both with concentrations of 1 $mol.l^{-1}$, for example. Alternatively, it may be a mixture of water and ethyl alcohol with a substantial conductance due to the presence of ions such as sodium or potassium (for example with concentrations of 0.1 $mol.l^{-1}$). Second fluid medium 142, for example, may comprise silicone oil that is insensitive to electric fields. Beneficially, the speed of sound in first fluid medium 141 may be 1480 m/s, while the speed of sound in second fluid medium 142 may be 1050 m/s.

Beneficially, first electrode 150 is provided in housing 110 so as to be in contact with the one of the two fluid mediums 141, 142 that is electrically conducting, In the example of FIGS. 1A-B, it is assumed the fluid medium 141 is the electrically conducting fluid medium, and fluid medium 142 is the substantially non-electrically conducting fluid medium. However it should be understood that fluid medium 141 could be the substantially non-electrically conducting fluid medium, and fluid medium 142 could be the electrically conducting fluid medium. In that case, first electrode 150 would be arranged to be in contact with fluid medium 142. Also in that case, the concavity of the contact meniscus as shown in FIGS. 1A-B would be reversed.

Meanwhile, second electrode 160*a* is provided along a lateral (side) wall of housing 110. Optionally, two or more second electrodes 160*a*, 160*b*, etc., are provided along a lateral (side) wall (or walls) of housing 110. Electrodes 150 and 160*a* are connected to two outputs of a variable voltage supply (not shown in FIGS. 1A-B).

Operationally, variably-refracting acoustic lens elements 10 operate in conjunction with acoustic transducer elements 20 as follows. In the exemplary embodiment of FIG. 1A, when the voltage applied between electrodes 150 and 160 by the variable voltage supply is zero, then the contact surface between first and second fluid media 141 and 142 is a meniscus M1. In a known manner, the shape of the meniscus is determined by the surface properties of the inner side of the lateral wall of the housing 110. Its shape is then approximately a portion of a sphere, especially for the case of substantially equal densities of both first and second fluid media 141 and 142. Because the acoustic wave W has different propagation velocities in first and second fluid media 141 and 142, the volume V filled with first and second fluid media 141 and 142 acts as a convergent lens on the acoustic wave W. Thus, the divergence of the acoustic wave W entering probe 100 is reduced upon crossing the contact surface between first and second fluid media 141 and 142. The focal length of variably-refracting acoustic lens element 10 is the distance from the corresponding acoustic transducer element 20 to a source point of the acoustic wave, such that the acoustic wave is made planar by the lens variably-refracting acoustic lens element 10 before impinging on acoustic transducer element 20.

When the voltage applied between electrodes 150 and 160 by the variable voltage supply is set to a positive or negative value, the shape of the meniscus is altered, due to the electrical field between electrodes 150 and 160. In particular, a force is applied on the part of first fluid medium 141 adjacent the contact surface between first and second fluid media 141 and 142. Because of the polar behavior of first fluid medium 141, it tends to move closer to or further away to electrode 160, depending on the sign of the applied voltage, as well as on the actual fluids that are used. Accordingly, the contact surface between the first and second fluid media 141 and 142 changes as illustrated in the exemplary embodiment of FIG. 1B. In FIG. 1B, M2 denotes the shape of the contact surface when the voltage is set to a non-zero value. Such electrically-controlled change in the form of the contact surface is called electrowetting. In case first fluid medium 141 is electrically conductive, the change in the shape of the contact surface between first and second fluid media 141 and 142 when voltage is applied is the same as previously described. Because of the change in the form of the contact surface, the focal length of variably-refracting acoustic lens element 10 is changed when the voltage is non-zero.

As seen in FIG. 1B, each of the variably-refracting acoustic lens elements 10 is individually controllable by applying selected voltages to the electrodes 150, 160*a* and 160*b* thereof. Thus, in the example of FIG. 1B, the first two variably-refracting acoustic lens elements 10 shown in the left have a voltage applied to their electrodes 150, 160*a* and 160*b* so as to change the contact surface to the shape M2, while the last variably-refracting acoustic lens element 10 shown to the far right in FIG. 1B has zero volts applied thereto and the contact surface thereof has the shape M1. Of course a wide variety of voltage combinations may be applied to the electrodes 150, 160*a* and 160*b* of the array of variably-refracting acoustic lens elements 10 so as to produce an almost infinite combination of contact surface shapes (including shapes other than M1 and M2) for the variably-refracting acoustic lens elements 10. This provides tremendous flexibility in focusing an acoustic beam for acoustic probe 100.

Beneficially, in the example of FIGS. 1A-B, in a case where fluid medium 141 consists primarily of water, then at least the bottom wall of housing 110 is coated with a hydrophilic coating 170. Of course in a different example where fluid medium 142 consists primarily of water, then instead the top wall of housing 110 may be coated with a hydrophilic coating 170 instead.

Meanwhile, PCT Publication WO2004051323, which is incorporated herein by reference in its entirety as if fully set forth herein, provides a detailed description of tilting the meniscus of a variably-refracting fluid lens.

Adjustment of variably-refracting acoustic lens element 10 can be controlled by external electronics (e.g., a variable voltage supply) that, for example, can adjust the surface topology within 20 ms when variably-refracting acoustic lens element 10 has a diameter of 3 mm, or as quickly as 100 microseconds when variably-refracting acoustic lens 10 has a diameter of 100-microns. When acoustic probe 100 operates in both a transmit mode and a receive mode, then variably-refracting acoustic lens elements 10 will be adjusted to alter the effective transmit and receive focusing. In a transmitting mode, transducer 15 comprising transducer elements 20 will be able to send out short time (broad-band) signals operated in M-mode, possibly short tone-bursts to allow for pulse wave Doppler or other associated signals for other imaging techniques. A typical application might be to image a plane with a fixed focus adjusted to the region on clinical interest. Another use might be to image a plane with multiple foci, adjusting the focus to maximize energy delivered to regions of axial focus. The ultrasonic signal can be a time-domain resolved signal such as normal echo, M-mode or PW Doppler or even a non-time domain resolved signal such as CW Doppler Beneficially, as explained in greater detail below, the combination of variably-refracting acoustic lens element 10 coupled to acoustic transducer 20 can replace a traditional 1D transducer array, with the added benefits of real-time adjustment of the elevation focus to make possible delivery of maximal energy at varying depths with the desired elevation focusing.

Often, an acoustic probe requires a variably-refracting acoustic lens having a medium scale (e.g., 4-10 $cm^2$) aperture, for example to provide a smaller focal spot, and at the same time exhibiting a smoothly varying time-delay, or phase, of the pressure field across the aperture in order to avoid grating lobes. In that case, there is a trade-off between the critical damping time (on the order of a few ms for a lens on the order of a few mm) and the size of the variably-refracting acoustic lens. Once the variably-refracting acoustic lens becomes too large, other effects such as gravity, inertia-related meniscus deformation due to lens movement, and other adverse properties begin to dominate. Current technology requires a diameter less than about 10 mm in diameter to achieve stability.

One approach to solve this problem is to group a collection of smaller variably-refracting acoustic lens elements together in such a way as to construct a larger effective aperture. In order for this to work most effectively, the larger aperture must appear to operate as a smoothly varying single variably-refracting acoustic lens. This requirement implies that the variably-refracting acoustic lens array—comprising a plurality of smaller variably-refracting acoustic lens elements—must be "space-filling" or have close to 100% packing.

Figure 2A:
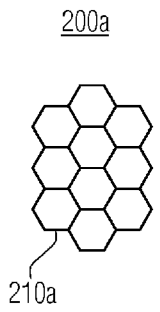
Figure 2B:
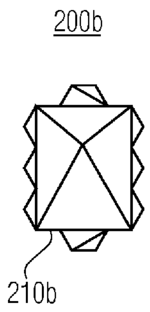
Figure 2C:
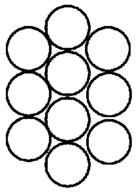

FIGS. 2A-C illustrate some possible arrangements of variably-refracting acoustic lens arrays.

FIG. 2C illustrates a variably-refracting acoustic lens array having a non-space-filling arrangement, as seen by the large amount of space between adjacent variably-refracting acoustic lens elements.

In contrast, FIGS. 2A-B show two exemplary embodiment of space-filling variably-refracting acoustic lens arrays.

FIG. 2A shows a variably-refracting acoustic lens 200*a* comprising a space-filling array of variably-refracting acoustic lens elements 210*a* each having the shape of a hexagon. This allows for full—or essentially full—spatial packing of variably-refracting acoustic lens elements 210*a* while simplifying the electronics and manufacturing process, as each variably-refracting acoustic lens element is identical to its neighbor.

FIG. 2B shows an alternative variably-refracting acoustic lens 200*b* comprising an array of variably-refracting acoustic lens elements 210*b* each having the shape of a triangle. In the illustrated case of the use of triangles, the advantage is a reduced count of lens elements 210*b* at the expense of making them all uniquely shaped and positioned. However, the same geometry in FIG. 2B instead can be covered with identically shaped triangles at the expense of more lens elements.

In both FIGS. 2A-B, full spatial coverage is achieved with the exception of the necessary space taken by the controlling electrodes. This space can be minimized by the use of thin conductors and the likely ultrasonic interference may be minimized by the lack of symmetry in the layout of these obstructive pieces (as shown in FIG. 2B). The overall effect of these conductors is expected to be minimal. Other alternative space-filling patterns can be constructed using lens elements having the shapes of concentric rings, squares, and other, more exotic patterns such as Penrose tiles.

Figure 3:
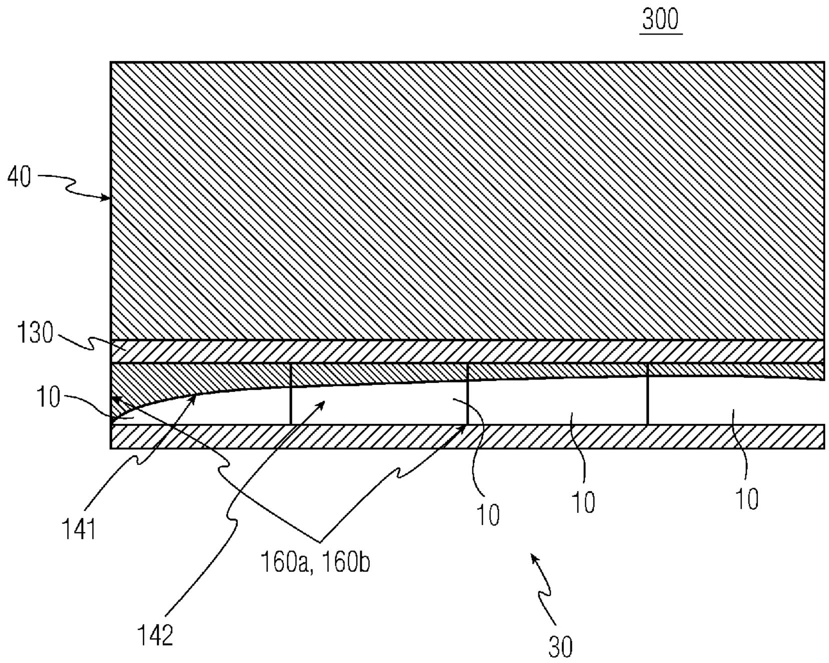
FIG. 3 shows one embodiment of an acoustic probe including a space-filling variably-refracting acoustic lens array coupled to an acoustic transducer having a single transducer element, or coupled to an acoustic transducer having a plurality of transducer elements which number fewer than the number of lenses.

FIG. 3 shows one embodiment of an acoustic probe 300 including a space-filling variably-refracting acoustic lens 30 coupled to an acoustic transducer 40. Variably-refracting acoustic lens 30 comprises an array of variably-refracting acoustic lens elements 10 and may be configured, for example, as shown in FIG. 2A or FIG. 2B. Each variably-refracting acoustic lens element 10 may be constructed essentially the same as described above with respect to FIG. 1, and so a detailed description thereof is not repeated here. Acoustic transducer 40 can be a single element transducer as illustrated in FIG. 3, or alternatively could be a 1D transducer array or a 2D transducer array.

FIG. 3 illustrates the ability to apply a different signal to the electrodes each variably-refracting acoustic lens element 10 to construct an effectively-larger, smoothly-varying variably-refracting acoustic lens 30. However, the effectively-larger meniscus needs not to be continuous. For example, there could be a vertical displacement from compartment to compartment. This is the same principle that is used for a Fresnel-lens. Ideally the coupling fluid 142 has a similar impedance to the layer in contact with a patient. When the surface reaches the correct topology, then acoustic transducer 40 will be excited, for example with either a short time imaging pulse for time-resolved echo information in traditional ultrasound imaging, or a time-resolved tone burst to allow for detection of motion along a line of site.

Figure 4:
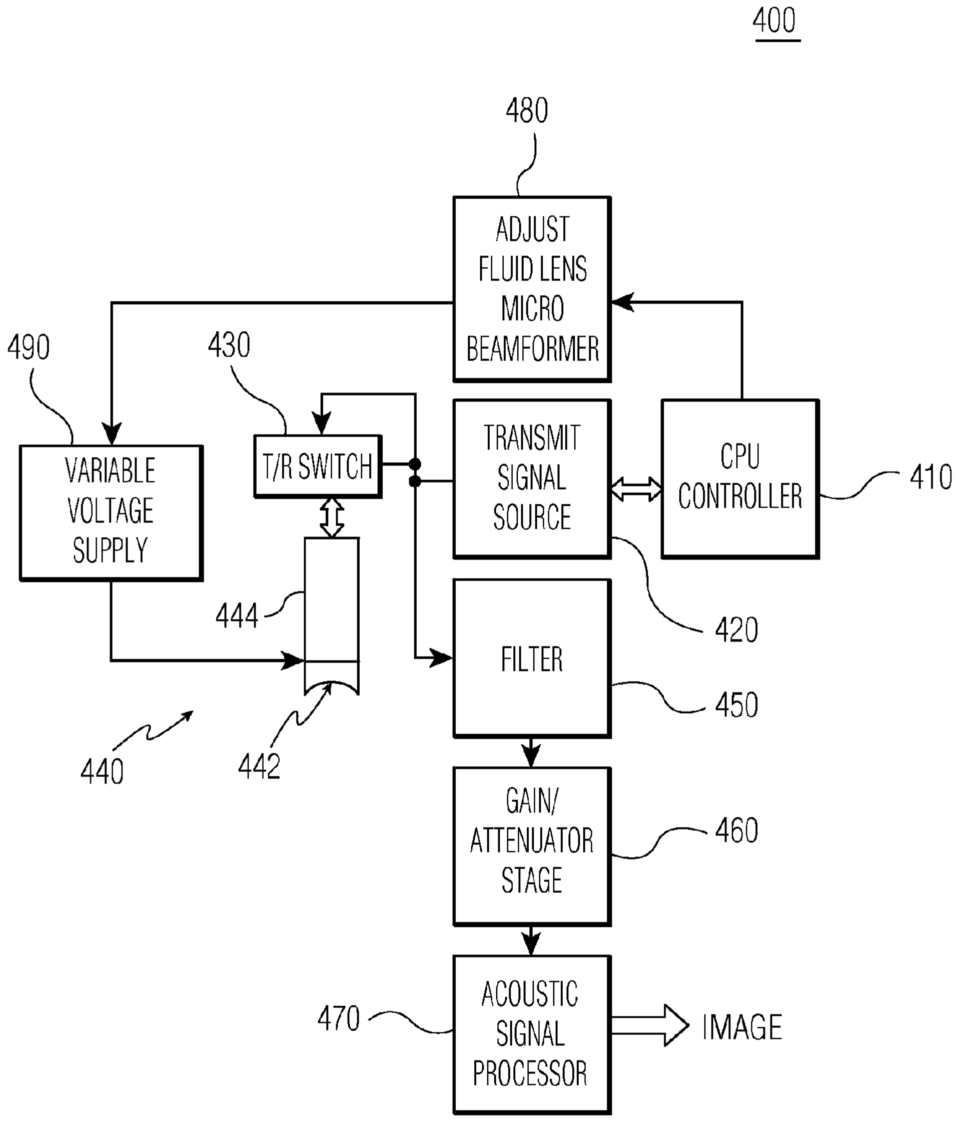
FIG. 4 shows a block diagram of an embodiment of an acoustic imaging apparatus.

FIG. 4 is a block diagram of an embodiment of an acoustic imaging apparatus 400 using an acoustic probe including a variably-refracting acoustic lens coupled to an acoustic transducer to provide real-time elevation focus control. Acoustic imaging apparatus 400 includes processor/controller 410, transmit signal source 420, transmit/receive switch 430, acoustic probe 440, filter 450, gain/attenuator stage 460, acoustic signal processing stage 470, elevation focus controller 480, and variable voltage supply 490. Meanwhile, acoustic probe 440 includes a plurality of variably-refracting acoustic lens elements 442 coupled to an acoustic transducer 444 comprising one or more transducer elements.

Acoustic probe 440 may be realized, for example, as acoustic probe 100 as described above with respect to FIG. 1, or acoustic probe 300 as illustrated in FIG. 3. In that case, beneficially the two fluids 141, 142 of each variably-refracting acoustic lens element 442 have matching impedances, but differing speed of sounds. This would allow for maximum forward propagation of the acoustic wave, while allowing for control over the direction of the beam. Beneficially, fluids 141, 142 have a speed of sound chosen to maximize flexibility in the focusing and refraction of the acoustic wave.

Variable voltage supply 490 supplies controlling voltages to electrodes of each variably-refracting acoustic lens element 442.

Beneficially, acoustic transducer 444 comprises a 1D array of acoustic transducer elements.

Operationally, acoustic imaging apparatus 400 operates as follows.

Elevation focus controller 480 controls voltages applied to electrodes of variably-refracting acoustic lens elements 442 by variable voltage supply 490. As explained above, this in turn controls a refraction of each variably-refracting acoustic lens element 442 as desired. In one embodiment, voltages are supplied to variably-refracting acoustic lens elements 442 such that a plurality of variably-refracting acoustic lens elements 442 operate together as a single variably refracting acoustic lens having an effective size greater than each one of the variably-refracting acoustic lens elements 442 (e.g., see FIG. 3 described above).

When the surface of the meniscus defined by the two fluids in variably-refracting acoustic lens elements 442 reach the correct topology, then processor/controller 410 controls transmit signal source 420 to generate one or more desired electrical signals to be applied to acoustic transducer 444 to generate a desired acoustic wave. In one case, transmit signal source 420 may be controlled to generate short time (broadband) signals operating in M-mode, possibly short tone-bursts to allow for pulse wave Doppler or other associated signals for other imaging techniques. A typical use might be to image a plane with a fixed elevation focus adjusted to the region of clinical interest. Another use might be to image a plane with multiple foci, adjusting the elevation focus to maximize energy delivered to regions of axial focus. The acoustic signal can be a time-domain resolved signal such as normal echo, M-mode or PW Doppler or even a non-time domain resolved signal such as CW Doppler.

In the embodiment of FIG. 2, acoustic probe 440 is adapted to operate in both a transmitting mode and a receiving mode. As explained above, in an alternative embodiment acoustic probe 440 may instead be adapted to operate in a receive-only mode. In that case, a transmitting transducer is provided separately, and transmit/receive switch 430 may be omitted.

Figure 5:
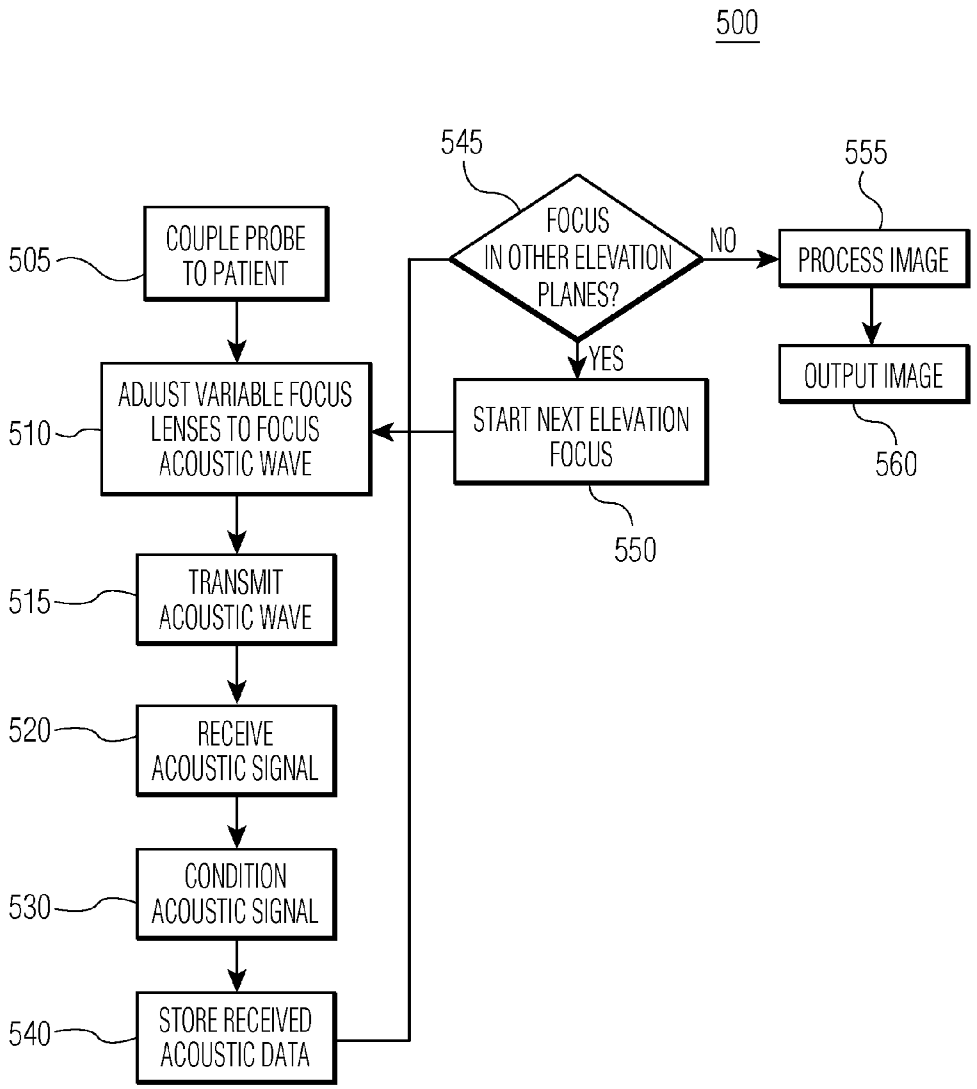
FIG. 5 shows a flowchart of one embodiment of a method of controlling an acoustic imaging apparatus.

FIG. 5 shows a flowchart of one embodiment of a method 500 of controlling the elevation focus of acoustic imaging apparatus 400 of FIG. 4.

In a first step 505, the acoustic probe 440 is coupled to a patient.

Then, in a step 510, elevation focus controller 480 controls a voltage applied to electrodes of variably-refracting acoustic lens elements 442 by variable voltage supply 490 to focus at a target elevation. As explained above, this in turn controls a refraction of each variably-refracting acoustic lens element 442 as desired. In one embodiment, voltages are supplied to variably-refracting acoustic lens elements 442 such that a plurality of variably-refracting acoustic lens elements 442 operate together as a single variably refracting acoustic lens having an effective size greater than each one of the variably-refracting acoustic lens elements 442 (e.g., see FIG. 3 described above).

Next, in a step 515, processor/controller 410 controls transmit signal source 420 and transmit/receive switch 430 to apply one or more desired electrical signals to acoustic transducer 444. Variably-refracting acoustic lens elements 442 operate in conjunction with acoustic transducer 444 to generate an acoustic wave and focus the acoustic wave in a target area of the patient, including the target elevation.

Subsequently, in a step 520, variably-refracting acoustic lens elements 442 operate in conjunction with acoustic transducer 444 to receive an acoustic wave back from the target area of the patient. At this time, processor/controller 410 controls transmit/receive switch 430 to connect acoustic transducer 444 to filter 450 to output an electrical signal(s) from acoustic transducer 444 to filter 450.

Next, in a step 530, filter 450, gain/attenuator stage 460, and acoustic signal processing stage 470 operate together to condition the electrical signal from acoustic transducer 444, and to produce therefrom received acoustic data.

Then, in a step 540, the received acoustic data is stored in memory (not shown) of acoustic signal processing stage 470 of acoustic imaging apparatus 400.

Next, in a step 545, processor/controller 410 determines whether or not it to focus in another elevation plane. If so, then the in a step 550, the new elevation plane is selected, and process repeats at step 510. If not, then in step 555 acoustic signal processing stage 470 processes the received acoustic data (perhaps in conjunction with processor/controller 410) to produce and output an image.

Finally, in a step 560, acoustic imaging apparatus 400 outputs the image.

In general, the method 500 can be adapted to make measurements where the acoustic wave is a time-domain resolved signal such as normal echo, M-mode or PW Doppler, or even a non-time domain resolved signal such as CW Doppler.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

The invention claimed is:

1. An acoustic imaging apparatus, comprising:

an acoustic probe including an acoustic transducer, and a plurality of variably-refracting acoustic lens elements coupled to the acoustic transducer, each variably-refracting acoustic lens element having at least a pair of electrodes operably configured to adjust at least one characteristic of the variably-refracting acoustic lens element in response to a selected voltage applied across the electrodes thereof;

an acoustic signal processor coupled to the acoustic transducer;

a variable voltage supply operably configured to apply selected voltages to the pair of electrodes of each variably-refracting acoustic lens element; and a controller operably configured to control the variable voltage supply to apply the selected voltages to the pairs of electrodes, wherein the acoustic transducer comprises a plurality of acoustic transducer elements, and wherein the variably-refracting acoustic lens elements are each coupled to a corresponding one of the acoustic transducer elements.

2. The acoustic imaging apparatus of claim 1, further comprising:

a transmit signal source; and a transmit/receive switch operably configured to selectively couple the acoustic transducer to the transmit signal source and to the acoustic signal processor.

3. The acoustic imaging apparatus of claim 1, wherein the at least one characteristic of the variably-refracting acoustic lens elements that is adjusted in response to the selected voltage applied across the electrodes includes a focus and tilt of the variably-refracting acoustic lens.

4. The acoustic imaging apparatus of claim 1, where the variably-refracting acoustic lens elements are controlled to operate as a single variably refracting acoustic lens having an effective size greater than each one of the variably-refracting acoustic lens elements.

5. The acoustic imaging apparatus of claim 4, wherein the variably-refracting acoustic lens elements comprise a space-filling array, where each of the variably-refracting acoustic lens elements has a shape of a hexagon, triangle, rectangle, square, polygon, or smoothly varying contour.

6. The acoustic imaging apparatus of claim 1, wherein each variably-refracting acoustic lens element comprises:

a cavity;

first and second fluid media disposed within the cavity; and the first and second electrodes, wherein a speed of sound of an acoustic wave in the first fluid medium is different than a corresponding speed of sound of the acoustic wave in the second fluid medium, wherein the first and second fluid media are immiscible with respect to each other, and wherein the first fluid medium has a substantially different electrical conductivity than the second fluid medium.

7. The acoustic imaging apparatus of claim 6, wherein the first and second fluid media have equal densities.

8. The acoustic imaging apparatus of claim 6, wherein each variably-refracting acoustic lens element includes a housing defining the cavity, and wherein a first one of the pair of electrodes is provided at a bottom or top of the housing, and a second one of the pair of electrodes is provided at a lateral side wall of the housing.

9. The acoustic imaging apparatus of claim 6, wherein a first one of the pair of electrodes is provided in contact with the one of the first and second fluid media having the greater electrical conductivity, and a second one of the pair of electrodes is isolated from the first and second fluid media having the greater electrical conductivity.

10. An acoustic probe, comprising:

an acoustic transducer; and a plurality of variably-refracting acoustic lens elements coupled to the acoustic transducer, each variably-refracting acoustic lens element having at least a pair of electrodes operably configured to adjust at least one characteristic of the variably-refractinc acoustic lens element in response to a selected voltage applied across the electrodes, wherein the acoustic transducer comprises a plurality of acoustic transducer elements, and wherein the variably-refracting acoustic lens elements are each coupled to a corresponding one of the acoustic transducer elements.

11. The acoustic probe of claim 10, wherein the at least one characteristic of the variably-refracting acoustic lens elements that is adjusted in response to the selected voltage applied across the electrodes includes a focus and elevation of the variably-refracting acoustic lens.

12. The acoustic probe of claim 10, where the variably-refracting acoustic lens elements are controlled to operate as a single variably refracting acoustic lens having an effective size greater than each variably-refracting acoustic lens element.

13. The acoustic probe of claim 12, wherein the variably-refracting acoustic lens elements comprise a space-filling array, where each of the variably-refracting acoustic lens elements has a shape of a hexagon, triangle, rectangle, square, polygon, or smoothly-varying contour.

14. The acoustic probe of claim 10, wherein each variably-refracting acoustic lens element comprises:

a cavity;

first and second fluid media disposed within the cavity; and the pair of electrodes, wherein a speed of sound of an acoustic wave in the first fluid medium is different than a corresponding speed of sound of the acoustic wave in the second fluid medium, wherein the first and second fluid media are immiscible with respect to each other, and wherein the first fluid medium has a substantially different electrical conductivity than the second fluid medium.

15. The acoustic probe of claim 14, wherein the first and second fluid media have equal densities.

16. The acoustic probe of claim 14, wherein each variably-refracting acoustic lens element includes a housing defining the cavity, and wherein a first one of the pair of electrodes is provided at a bottom or top of the housing, and a second one of the pair of electrodes is provided at a lateral side wall of the housing.

17. The acoustic probe of claim 14, wherein a first one of the pair of electrodes is provided in contact with the one of the first and second fluid media having the greater electrical conductivity, and a second one of the pair of electrodes is isolated from the first and second fluid media having the greater electrical conductivity.

18. A method of performing a measurement using acoustic waves, the method comprising: (1) applying an acoustic probe to a patient, the probe comprising an acoustic transducer and a plurality of variably-refracting acoustic lens elements coupled to the acoustic transducer, each variably-refracting acoustic lens element having at least a pair of electrodes operably configured to adjust at least one characteristic of the variably-refracting acoustic lens element in response to a selected voltage applied across the electrodes, the acoustic transducer further comprising a plurality of acoustic transducer elements, the variably-refracting acoustic lens elements being each coupled to a corresponding one of the acoustic transducer elements; (2) controlling the plurality of variably-refracting acoustic lens elements of the acoustic probe to focus in a desired focus; (3) receiving from the variably-refracting acoustic lens elements, at the acoustic transducer, an acoustic wave back coming from a target area corresponding to the desired focus; and (4) outputting from the acoustic transducer an electrical signal corresponding to the received acoustic wave.

19. The method of claim 18, further comprising, prior to step (3), applying one or more electrical signals to the acoustic transducer coupled to the variably-refracting acoustic lens elements to generate an acoustic wave focused in the desired focus.

20. The method of claim 18, wherein controlling the plurality of variably-refracting acoustic lens elements to focus in a target region, includes applying voltages to electrodes of each of the variably-refracting acoustic lens elements so as to displace two fluids disposed in a housing of the variably-refracting acoustic lens elements with respect to each other, wherein the two fluids have different acoustic wave propagation velocities with respect to each other.

21. The method of claim 18, wherein controlling the plurality of variably-refracting acoustic lens elements of the acoustic probe to focus in a desired elevation focus comprises controlling the variably-refracting acoustic lens elements to operate as a single variably refracting acoustic lens having an effective size greater than each one of the variably-refracting acoustic lens elements.

22. The method of claim 18, further comprising:

(5) producing received acoustic data from the electrical signal output by the transducer.

23. The method of claim 22, further comprising:

(6) storing the received acoustic data into memory; (7) determining whether or not to focus at another focus; (8) when another focus is selected; repeating steps (1) through (7) for the new focus; and (9) when no more foci are selected, processing the stored acoustic data and outputting an image from the processed acoustic data.

* * * * *